United States Patent
Orth

(10) Patent No.: US 8,483,857 B2
(45) Date of Patent: Jul. 9, 2013

(54) BLANK AND DATABASE OF PREFABRICATED PARTIAL SURFACES OF DENTAL PROSTHETICS

(75) Inventor: Ulrich Orth, Heppenheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 1249 days.

(21) Appl. No.: 12/299,895

(22) PCT Filed: May 8, 2007

(86) PCT No.: PCT/EP2007/054423
§ 371 (c)(1),
(2), (4) Date: Nov. 6, 2008

(87) PCT Pub. No.: WO2007/128811
PCT Pub. Date: Nov. 15, 2007

(65) Prior Publication Data
US 2009/0181346 A1    Jul. 16, 2009

Related U.S. Application Data

(60) Provisional application No. 60/798,297, filed on May 8, 2006.

(30) Foreign Application Priority Data

May 8, 2006  (DE) .......................... 10 2006 021 640

(51) Int. Cl.
*G06F 19/00* (2011.01)
(52) U.S. Cl.
USPC ................. 700/97; 700/60; 700/61; 700/171; 700/98; 700/118
(58) Field of Classification Search
None
See application file for complete search history.

(56) References Cited

U.S. PATENT DOCUMENTS 3,004,343 A    10/1961  Rydin ........................ 433/203.1
4,742,464 A *  5/1988  Duret et al. ................... 700/183
(Continued)

FOREIGN PATENT DOCUMENTS

CA    2 531 624        1/2005
DE    296 21 807 U1    2/1997
(Continued)

OTHER PUBLICATIONS

Form PCT/ISA/220, Form PCT/ISA/210 and Form PTO/ISA/237 of International Application PCT/EP2007/054423.

*Primary Examiner* — Kavita Padmanabhan
*Assistant Examiner* — Christopher E Everett
(74) *Attorney, Agent, or Firm* — Fitzpatrick, Cella, Harper & Scinto

(57) ABSTRACT

A method for producing a dental prosthetic item, including providing a 3D model of the item. The providing includes determining an esthetically relevant designed subregion of a 3D model of the item as part of an exterior surface of the item. The subregion corresponds to a labial surface and/or incisor edge, or to a buccal and/or occlusal surface. Further steps include selecting a suitable blank, specifying a blank having a prefabricated esthetically relevant terminal subsurface of a surface of a tooth, a terminal subsurface of the blank being such as at least approximates the subregion. A further step includes forming the item from the selected blank such that a prefabricated terminal subsurface of the blank remains unmachined in at least a central region thereof. The forming includes machining the blank only in a marginal area of the terminal subsurface and on at least some surfaces outside of the terminal subsurface.

15 Claims, 9 Drawing Sheets

U.S. PATENT DOCUMENTS

| | | | |
|---|---|---|---|
| 5,092,022 A * | 3/1992 | Duret | 29/896.1 |
| 5,151,044 A * | 9/1992 | Rotsaert | 433/229 |
| 5,383,752 A | 1/1995 | Rheinberger et al. | 409/105 |
| 5,691,905 A | 11/1997 | Dehoff et al. | 364/468.04 |
| 5,813,859 A * | 9/1998 | Hajjar et al. | 433/223 |
| 5,827,063 A | 10/1998 | Greenstein | 433/213 |
| 6,641,340 B1 * | 11/2003 | Hajjar et al. | 409/94 |
| 6,957,118 B2 * | 10/2005 | Kopelman et al. | 700/118 |
| 6,979,496 B2 * | 12/2005 | Haymann et al. | 428/542.8 |
| 7,112,065 B2 * | 9/2006 | Kopelman et al. | 433/213 |
| 7,228,191 B2 * | 6/2007 | Hofmeister et al. | 700/98 |
| 7,383,094 B2 * | 6/2008 | Kopelman et al. | 700/118 |
| 7,623,942 B2 * | 11/2009 | Touchstone | 700/182 |
| 7,698,014 B2 * | 4/2010 | Dunne et al. | 700/118 |
| 7,735,542 B2 * | 6/2010 | Marshall et al. | 164/35 |
| 7,738,989 B2 * | 6/2010 | Taub et al. | 700/117 |
| 7,762,814 B2 * | 7/2010 | van der Zel | 433/201.1 |
| 7,774,080 B2 * | 8/2010 | Holzner et al. | 700/97 |
| 7,819,662 B2 * | 10/2010 | Marshall et al. | 433/218 |
| 7,901,209 B2 * | 3/2011 | Saliger et al. | 433/215 |
| 2002/0076530 A1 * | 6/2002 | MacDougald et al. | 428/195 |
| 2003/0031984 A1 * | 2/2003 | Rusin et al. | 433/215 |
| 2003/0138756 A1 | 7/2003 | Monkmeyer | 433/202.1 |
| 2004/0185422 A1 * | 9/2004 | Orth et al. | 433/213 |
| 2005/0196723 A1 | 9/2005 | Monkmeyer | 433/202.1 |
| 2006/0008774 A1 * | 1/2006 | Orth et al. | 433/202.1 |
| 2006/0008776 A1 * | 1/2006 | Orth et al. | 433/215 |
| 2006/0063135 A1 | 3/2006 | Mehl | 433/223 |
| 2006/0168815 A1 * | 8/2006 | Saliger et al. | 29/896.11 |
| 2006/0204932 A1 * | 9/2006 | Haymann et al. | 433/201.1 |
| 2007/0290385 A1 * | 12/2007 | Holzner et al. | 264/20 |

FOREIGN PATENT DOCUMENTS

| | | |
|---|---|---|
| DE | 198 14 762 A1 | 10/1998 |
| DE | 198 38 239 A1 | 3/2000 |
| DE | 100 05 354 A1 | 8/2001 |
| EP | 1088620 A1 * | 4/2001 |
| EP | 1 304 088 A1 | 4/2003 |
| EP | 1 454 596 A1 | 9/2004 |
| WO | WO 01/58378 A1 | 8/2001 |
| WO | WO 02/09612 A1 | 2/2002 |
| WO | WO 2004/044787 A2 | 5/2004 |
| WO | WO 2005/007007 | 1/2005 |
| WO | WO 2005/007007 A2 | 1/2005 |
| WO | WO 2007137837 A1 * | 12/2007 |

* cited by examiner

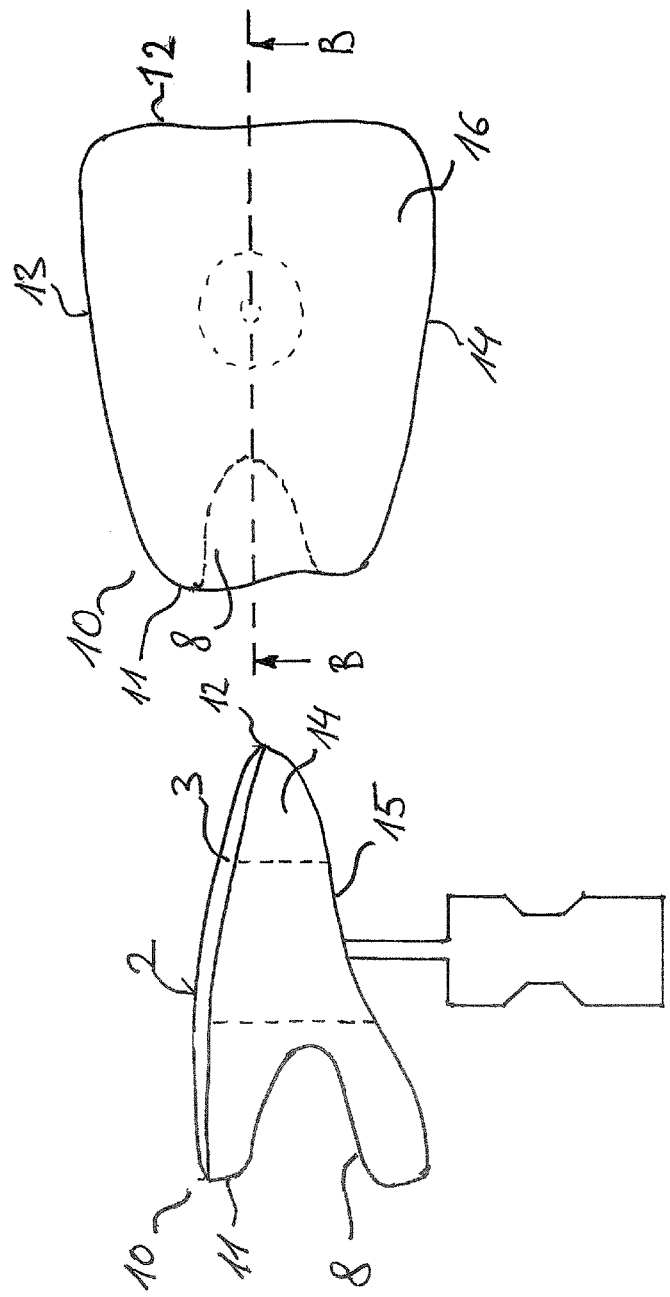

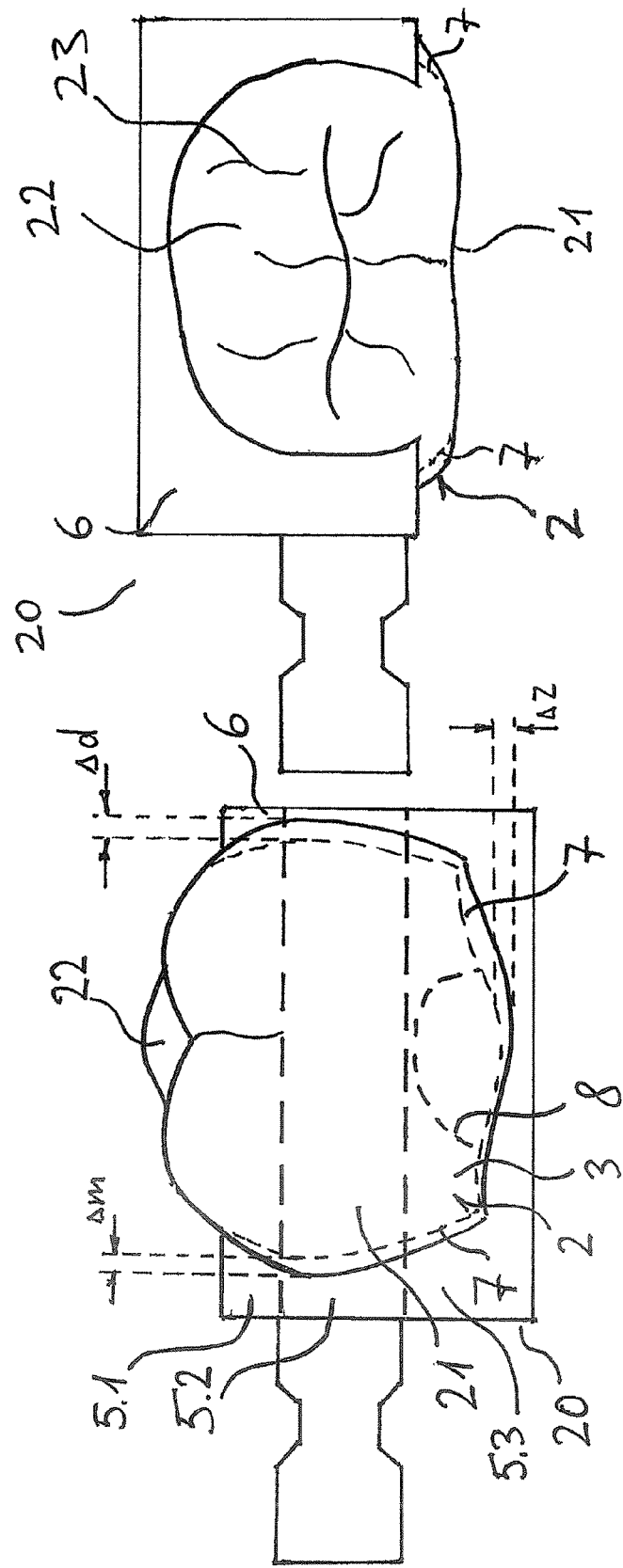

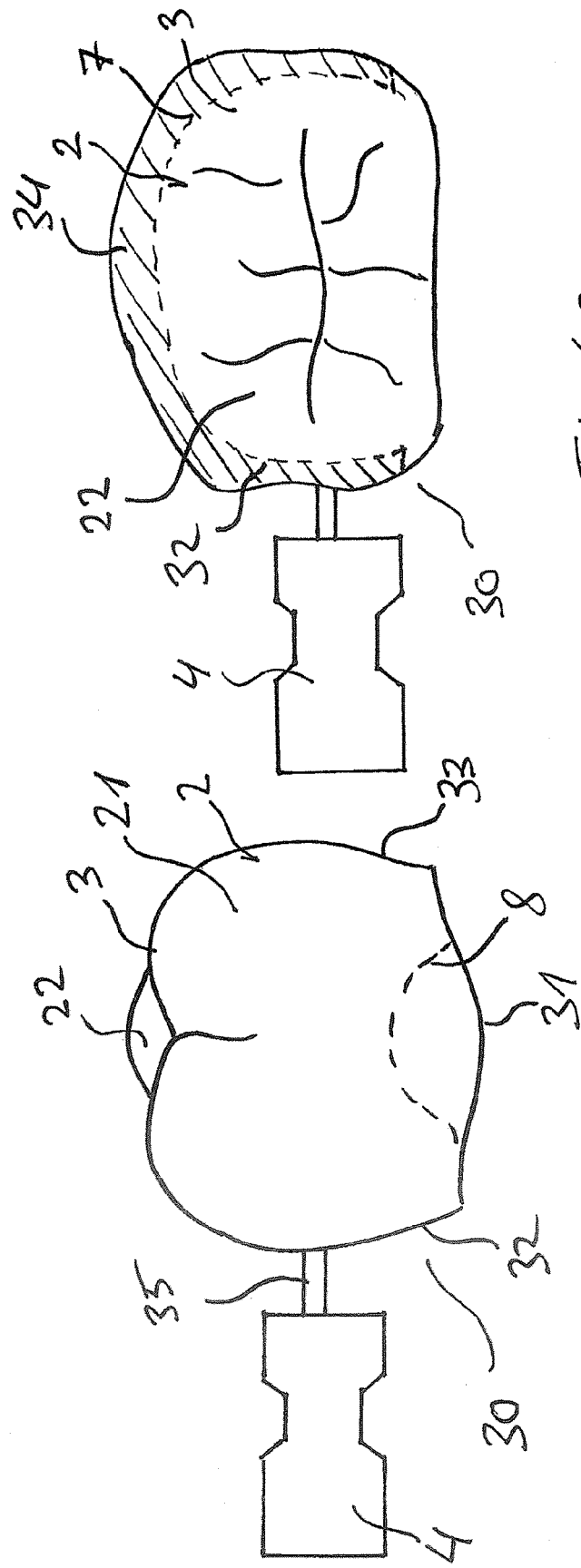

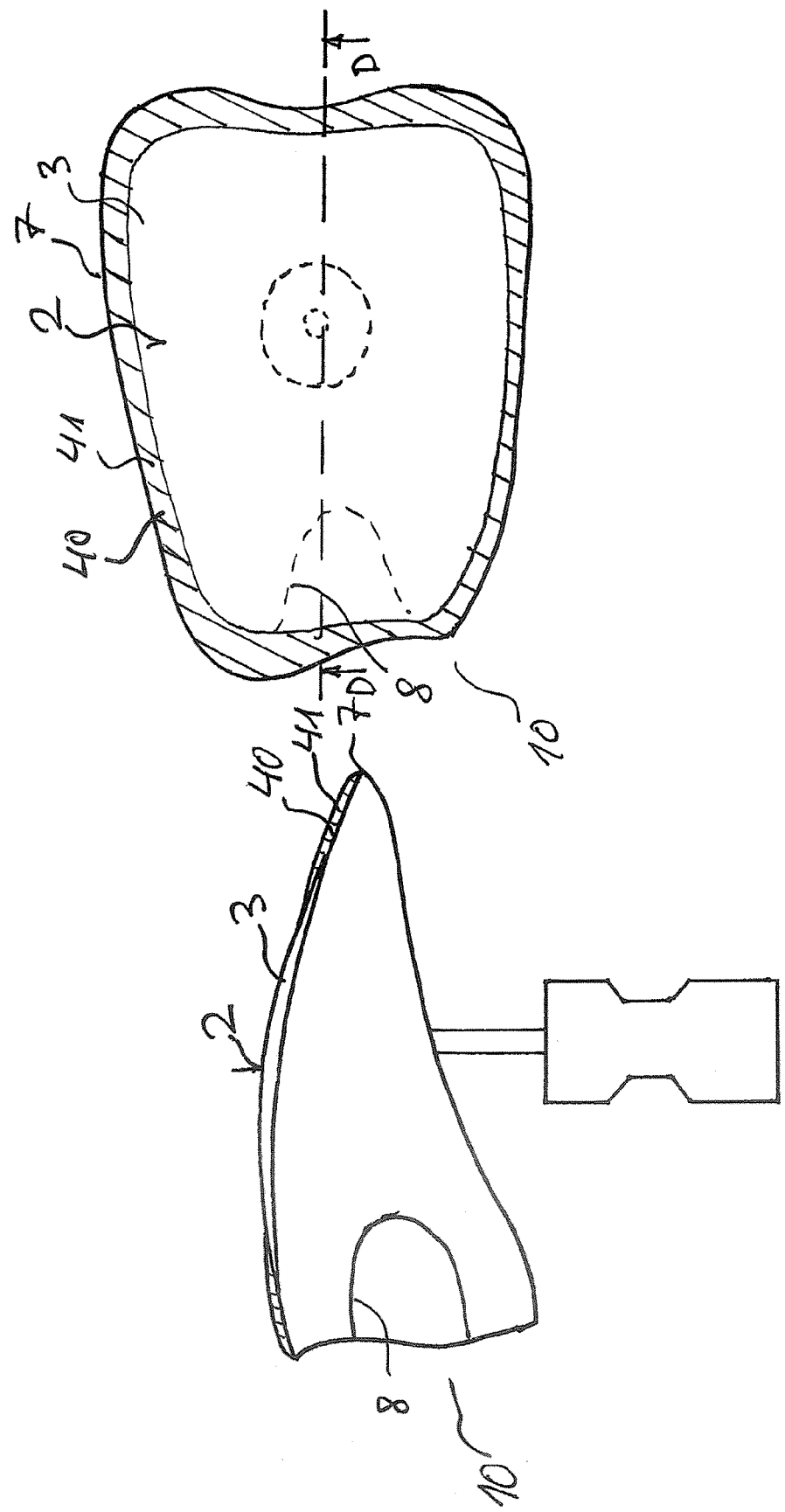

BLANK AND DATABASE OF PREFABRICATED PARTIAL SURFACES OF DENTAL PROSTHETICS

CROSS REFERENCE TO RELATED APPLICATIONS

This Application is a National Stage filing under 35 U.S.C. 371 of International Application No. PCT/EP2007/054423 filed May 8, 2007, which claims priority to German Patent Application No. 10 2006 021 640.7 and U.S. Provisional Patent Application No. 60/798,297, both filed May 8, 2006. Each of these applications is incorporated by reference herein its entirety, as if set forth fully herein.

TECHNICAL FIELD

The invention relates to a method and a blank for the production of dental prosthetic items on the basis of a 3D model of the dental prosthetic item to be produced. The blank has a prefabricated terminal subsurface whose geometry and surface attributes are in conformity with at least one subregion of the dental prosthetic item to be synthesized.

DESCRIPTION OF THE PRIOR ART

DE 100 05 354 A1 discloses a tooth assortment and a method for the preparation of teeth. The assortment of factory-made teeth has greater outside dimensions in the cervical region than a prepared tooth. Production is carried out by securing the prefabricated tooth in a device and correlating it virtually with the situation of the prepared tooth. Internal fitting to the prepared tooth is effected by excavating the lumen and external fitting by milling off material down to the preparation border to ensure that the blank accurately fits the prepared tooth.

This suffers from the drawback that the prefabricated teeth can only be fitted at the preparation border in the cervical region and there are thus no degrees of freedom for customizing the remaining exterior surface to the anatomical situation in the oral cavity of the patient.

The assortment of such prefabricated teeth must cover all possible variants as regards coloration and dental function to ensure that the prosthetic item matches in color and shape, which means that the assortment must contain a large number of prefabricated teeth in order to accommodate the diversity of all possible shapes and colorations of natural teeth.

The prosthetic item is prefabricated completely in a complex process.

In addition, it can be detrimental when the exterior surfaces of the prefabricated tooth in the region of the preparation border are only slightly oversize relative to the final shape of the prosthetic item to be produced. If checking of the position of the machining tool used is carried out only when contact with the material to be machined is made, for example, by detecting a change in the power consumption of an electric motor driving the machining tool, a position check is only possible just before reaching the final shape of the prefabricated tooth.

Frequently, the detection of a change in power consumption of the machining tool makes it also possible to ascertain whether the machining tool has broken and the electric motor is thus running in an idling state. Since only a small amount of material has to be removed in the cervical region, malfunction information may occur during the machining process even if the machining tool is not fractured but because the friction forces produced on the material to be machined are too low.

For this reason, a calibration member is provided in the prior art between the holder and the prefabricated tooth, the position of said calibration member relative to the tooth being known. Scanning the calibration member will then reveal the position of the tooth to be machined.

EP 1 454 596 A1 discloses a method for the production of veneers for dentures. The veneers exhibit thin-walled shells of plastics material having a colorizing layer applied thereto, and the transparency and the coloration of the veneers can be configured freely and independently on account of the multilayered design. The colorizing layer comprises a dye for coloration of transparent or translucent dentures. The veneer is applied to the surface of a dental prosthetic item and has a thickness of from 0.2 mm to 1.5 mm.

This suffers from the drawback that the attachment of the veneer to a dental prosthetic item while taking into consideration the planned translucency profile and coloration of the dental prosthetic item is time-consuming and requires great technical effort. Consequently, it is not possible to provide the patient with a dental prosthetic item during a single session.

DE 198 28 239 A1 discloses a system for the production of dental prosthetic items for prepared teeth, in which groups of blanks each have the same internal and external geometries, the external geometry of a blank designated for a crown having the same or almost the same outer shape as that of the tooth to be replaced.

The drawback here is that a very large assortment of blanks must be available for the purpose of finding a blank which matches the tooth and has the same outer shape.

DE 198 14 762 A1 discloses a method for the production of a dental prosthetic item using premolds based on impressions of real human teeth of various sizes.

This suffers from the drawback that the individual premolds forming the complete prosthesis can only be adapted to each other at their adjacent surfaces, but not at their exterior surfaces. As a result, a large number of premolds must be available in order to fulfill requirements of individual forms of denture.

DE 296 21 807 U1 discloses prefabricated partial crowns intended for damaged molars and premolars and adapted to cover damaged or prepared masticatory and/or lateral surfaces of said teeth to form sectors or semicircular segments thereon.

Such partial crowns are suitable for replacing a partially damaged tooth, but not the entire tooth.

U.S. Pat. No. 6,979,496 B2 discloses a blank database in which the exterior surface of the blanks is chosen such that final milling thereof produces a minimum amount of waste material.

This suffers from the drawback that with this method all surfaces of the dental prosthetic item must be carved from the blank by milling, which means that the esthetically relevant surfaces must be subsequently veneered to comply with the esthetic requirements of a dental prosthesis.

U.S. Pat. No. 5,691,905 A discloses a method for milling and polishing a set of dental moldings, by which synthetic teeth and families of synthetic teeth of various sizes and/or colorations but of similar shape are produced.

The disadvantage here is that the esthetically relevant surfaces must, after machining, be subsequently reworked in order to satisfy the esthetic requirements of a dental prosthesis.

It is thus an object of the present invention to provide dental prosthetic items that are produced without greater technical effort and with a relatively small assortment of blanks and which can be permanently inserted during the first session and which nevertheless adequately satisfies esthetic demands in comparison with a natural tooth.

SUMMARY AND OBJECTS OF THE INVENTION

This object is achieved by the features of the independent claim 1 concerning the method, 15 concerning the blank, 31 concerning the assortment of blanks, 32 concerning the tooth database and 34 concerning the database of blanks of the present invention.

In the present invention, a method for the production of a dental prosthetic item is proposed which comprises the provision of a 3D model of a dental prosthetic item and the selection of a suitable blank from a plurality of possible blanks.

The provision of the 3D model of the dental prosthetic item comprises the determination of an esthetically relevant designed subregion of the 3D model of the dental prosthetic item as part of an exterior surface of said dental prosthetic item, and a blank is specified from a plurality of blanks having a prefabricated esthetically relevant terminal subsurface of a surface of the tooth, the terminal subsurface of said blank being such as at least approximates the thus specified designed subregion. The 3D model of said dental prosthetic item is carved from the selected blank such that the prefabricated terminal subsurface of said blank remains unmachined in at least a central region thereof.

The 3D model of the dental prosthetic item is provided, for example, by design methods involving a digital dental prosthetic planning system so as to match it to the preparation site and is saved to a memory device for use in the method of the invention. The esthetically relevant designed subregion is a subregion of the specified designed 3D model which has been selected with respect to its position and shape. For example, an esthetically relevant designed subregion can be a surface which will later be visible from outside the oral cavity when the mouth is open and which should give a visual impression which, for esthetic reasons, should be similar to that of natural teeth.

The selection of the blank having a prefabricated terminal subsurface, which at least approximates the designed subregion, from a plurality of blanks can preferably take the form of a computer-aided selection from a plurality of 3D models of blanks stored in a memory device. The remaining surface of the blank is accordingly not prefabricated and will be machined to the final shape of the planned dental prosthetic item. Machining the selected blank can, for example, take place using computerized machining equipment following computation of a machining schedule.

In the method of the invention, it is accordingly possible to carve a large number of different dental prosthetic items from one type of blank having a specific terminal subsurface, which prosthetic items will, on the one hand, have designed subregions that are similar to said terminal subsurface and, on the other hand, show different external shapes in the region outside of said terminal subsurface. When manufacturing the blank, it is, unlike in the case of complete prefabrication, only necessary to pre-fabricate one particular terminal subsurface of esthetic significance, for example as regards shape, coloration, and translucency, so as to correspond to the planned dental prosthetic item. This simplifies the production process.

The production of the dental prosthetic item from the selected blank can be carried out separately from designing the dental prosthetic item, for example, in a dental technician's laboratory.

The terminal subsurface at least approximately similar to the designed subregion takes the place of the designed subregion. Thus the esthetic impression of the prefabricated terminal subsurface will be left unchanged as far as possible, but the external shape of the 3D model of the dental prosthetic item in the region of the esthetically relevant designed subregion will be replaced by at least one similar part of the terminal subsurface. The finished dental prosthetic item can thus deviate slightly from the specified digital 3D model of the planned dental prosthetic item in the region of the designed subregion because the prefabricated terminal subsurface will be left untouched during machining of the relevant region. If this designed subregion is, for example, a visible surface, the small deviation will have no effect on the accuracy of fit relative to the adjacent teeth.

Advantageously, the provision of the 3D model of the dental prosthetic item involves the selection of a 3D model of a tooth which matches the preparation site from a tooth database comprising a plurality of 3D models of a tooth having at least one specified esthetically relevant terminal subsurface. For each 3D model of a tooth in the tooth database there is present, in a database of blanks, a 3D model of a blank having a terminal subsurface which is coincident with the terminal subsurface of the tooth. The selected 3D model of the tooth is changed for adaptation thereof to the individual tooth situation at the preparation site, but the specified terminal subsurface remains unchanged in at least a central region thereof. Furthermore, there exists an assortment of blanks matching the database of blanks, and the 3D model of the dental prosthetic item is carved from the blank to correspond to the 3D model of the tooth.

The 3D models of the teeth in the tooth database and the corresponding 3D models of the blanks in the database of blanks and present in an assortment of blanks exhibit coincident terminal subsurfaces having specified border lines. The 3D model of the tooth is slightly changed but without altering at least the central region of the terminal subsurface, and there is produced a customized 3D model of the dental prosthetic item. Subsequently, the dental prosthetic item is carved from the corresponding blank in the assortment of blanks. The positional relationship between the designed subregion and the terminal subsurface is inherently given and must not be additionally determined, for the designed subregion is produced from the terminal subsurface of the 3D model of the tooth in the tooth database and is coincident with the designed subregion at least in the central region thereof. When the position of the blank in the machining equipment is known, it will be possible to draw up the machining schedule, because the positional relationship will be known.

An advantageous alternative comprises not specifying a designed subregion on the 3D model of the planned dental prosthetic item with reference to 3D models of teeth in a tooth database but to specify said designed subregion either interactively by the user using input means or automatically by a computer with reference to specified parameters. For example, the user can mark the designed subregion in a software application via input means such as a keyboard or mouse by, for example, drawing in the boundary line or carrying out a selection of predefined cells in the manner of a puzzle. The designed subregion can alternatively be specified by computer-aided automatic selection with reference to specified parameters. For example, the incident light and the visibility of the tooth surfaces can be computer-simulated and the specific partial area deemed to be visible be automatically defined as the designed subregion. The designed subregion may thus deviate slightly from a subregion of the terminal subsurface because the 3D model is provided without considering a tooth database exhibiting terminal subsurfaces.

Advantageously, the selection of a 3D model of a blank from a plurality of 3D models of blanks having at least one prefabricated terminal subsurface of a tooth surface and stored, for example, in a memory device can automatically be carried out by the computer. The deviations between the specified designed subregion on the 3D model of the dental prosthetic item and the prefabricated terminal subsurface are minimized. By this means a blank is selected whose terminal subsurface best corresponds to the designed subregion.

Advantageously, the 3D model of the dental prosthetic item is carved from the selected blank in such a manner that in the finished dental prosthetic item at least one subregion of the prefabricated terminal subsurface of the blank takes the place of the selected designed subregion of the 3D model of the dental prosthetic item. In this way the prefabricated terminal subsurface in the region similar to the designed subregion remains unmachined, although the finished dental prosthetic item will show slight deviations in that region from the 3D model of the planned dental prosthetic item. In the case of the esthetically relevant surfaces such as visible surfaces this does not lead to any mismatching of the dental prosthetic item, however.

Advantageously, minimization of the deviations is effected such that the deviations are mainly located in the marginal area of the designed subregion. The software compares the designed subregion with various subregions of the terminal subsurface, and the blank showing least deviations is selected. The deviations should be kept to the marginal area because the visual impression given by the marginal area is less significant.

Advantageously, a positional relationship between the specified designed subregion of the 3D model of the dental prosthetic item and the prefabricated terminal subsurface of the blank can be determined, in order to make the designed subregion of the 3D model of the dental prosthetic item to coincide with the similar subregion of the prefabricated terminal subsurface in the 3D model. This can be done by displaying the 3D model of the dental prosthetic item and carrying out visual inspection thereof within the 3D model of the selected blank. Positioning of the 3D model of the dental prosthetic item to effect coincidence can be carried out automatically by the software or manually by the user. The 3D model of the dental prosthetic item can, for example, be graphically displayed on a display unit within the 3D model of the blank and positioned by the user using input means, by which means the positional relationship will be determined.

Advantageously, a machining schedule for the selected blank can be drawn up with reference to said positional relationship. The machining schedule then takes into account both the surfaces that may not be machined and the surfaces which still have to be machined.

Advantageously, the blank may only be machined at points requiring machining in the marginal area of the terminal subsurface and outside the terminal subsurface. By this means at least the central region of the terminal subsurface is left untouched and accordingly has the esthetic surface attributes of the prefabricated terminal subsurface.

Advantageously, the blank can have a translucent layer and the prefabricated terminal subsurface can be disposed on the translucent layer. By this means the translucency attributes of natural teeth can be imitated and the esthetic impression improved.

Advantageously, the prefabricated terminal subsurface of the blank can comprise the designed subregion of the dental prosthetic item and the terminal subsurface disposed over the translucent layer can be machined except for the designed subregion. Subsequently, the machined edge of the translucent layer can be polished. By this means the property of translucency at the edges of the translucent layer which will have been reduced on account of the grinding operation will be regained.

Advantageously, the designed subregion of the dental prosthetic item can comprise the prefabricated terminal subsurface of the blank. The remaining marginal area between the prefabricated terminal subsurface and the designed subregion, which initially exhibits no translucent layer, can then be subsequently veneered with a translucent layer and polished. By this means the desired translucency property of the entire designed subregion is ensured in the marginal area also.

Advantageously, the surfaces to be machined outside the terminal subsurface of the blank can be oversized relative to the surface of the planned dental prosthetic item by at least 1 mm. Checking the position of a machining tool, for example, a grinder, is often carried out by contact thereof with the material to be machined. By this means it is possible to carry out a position check at least 1 mm before reaching the surface of the planned dental prosthetic item, making precision work possible. Furthermore, the machining tool can be moved within the blank during machining under a sufficiently large electrical load such that load-dependent control or monitoring is possible.

Advantageously, the specified designed subregion can correspond to a part of the surface that is visible from outside the oral cavity following placement of the dental prosthetic item in the oral cavity. For esthetic reasons, visible surfaces should be visually similar to natural teeth. This is achieved by selecting or specifying a visible surface as a designed subregion and carving said area from the prefabricated terminal subsurface of a blank giving a visual impression similar to that given by natural teeth.

Advantageously, the specified designed subregion of the planned dental prosthetic item can correspond, in the case of incisors, to the labial surface and preferably also to the incisor edge or, in the case of premolars, to the buccal surface and preferably also to the occlusal surface. The said surfaces are visible in normal daylight from outside when the mouth is open and should, for esthetic reasons, give a visual impression similar to that given by natural teeth as far as possible. Other surfaces, on the other hand, are of minor significance with respect to their esthetic impression.

In dentistry the following terms are used as indications of direction: occlusal means pertaining to the chewing surface of a premolar, labial means pertaining to the lip, buccal means pertaining to the cheek, mesial means toward the center line of the dental arch, distal means toward the end of the dental arch, incisal means toward the cutting edge of an incisor and cervical means toward the dental neck. A tooth accordingly has a lateral mesial surface, a lateral distal surface, in the case of incisors a labial surface facing the lip and an incisor edge, and in the case of premolars, a buccal surface facing the cheek and an occlusal surface. The mating surface of a dental prosthetic item is directed toward the dental neck and is referred to as a cervical surface.

The posterior premolars are only slightly visible in daylight from outside and there is therefore only limited necessity for any optical adaptation of the surface in the case of dental prosthetic items to be inserted at such locations. According to the International Tooth Numbering System, esthetic surfaces requiring adaptation to give the visual impression of natural teeth are considered to be the labial surfaces of anterior teeth 11-13, 21-23, 31-33, 41-43, the buccal surfaces and/or the occlusal surfaces of anterior premolars 14, 15, 24, 25, 34, 35, 44, 45, and the occlusal surfaces of posterior premolars 16-18, 26-28, 36-38, 46-48.

Advantageously, the specified designed subregion can not take up more than 50% of the entire exterior surface of the 3D model of the dental prosthetic item. By this means the manufacturing efforts of the blank are reasonable and there remain sufficient degrees of freedom to allow for the blank to be accurately machined to fit the individual anatomical situation in the oral cavity of the patient, while at least the central region of the prefabricated terminal subsurface is left untouched.

Advantageously, the blank can be selected from a large number of blanks having prefabricated terminal subsurfaces which vary as to their shape and/or coloration and/or translucency attributes. The translucent layer has a coloration and translucency similar to natural teeth. For this reason, it is necessary to present a large number of blanks having translucent layers which cover the manifold coloration and translucency attributes of various natural teeth.

A blank intended for the production of a dental prosthetic item has, according to the invention, a prefabricated terminal subsurface matching that of the planned dental prosthetic item with regard to its geometry and surface attributes. Outside the prefabricated esthetically relevant terminal subsurface, the blank possesses surfaces which are oversized relative to the surface of the given dental prosthetic item and which must be machined.

Such a blank offers sufficient degrees of freedom for machining outside the terminal subsurface or for machining the edge surfaces. In this way a plurality of different dental prosthetic items can be produced from one type of blank, by which means the number of blanks in any one assortment of blanks can be reduced.

Advantageously, the prefabricated terminal subsurface will not take up more than 50% of the entire surface of the blank. This area is sufficient to make it possible to machine the blank so as to match the anatomical situation in the oral cavity of the patient to provide an adequate esthetic quality in each individual case, and simultaneously to keep down the cost of prefabrication of the terminal subsurface.

Advantageously, the degree of oversize can be at least 1 mm. This makes it possible to carry out a position check of a machining tool in good time, when contact is made with the material, namely at a distance from the surface of the planned dental prosthetic item of at least 1 mm, in addition to load-dependent monitoring during machining.

Advantageously, the blank can have a translucent layer and the prefabricated terminal subsurface can be disposed on the trans-lucent layer. This makes it possible to carve a dental prosthetic item from the blank to provide an item which has translucency attributes similar to those of natural teeth.

Advantageously, the translucent layer has a thickness of from 0.3 mm to 1.5 mm and is preferably polished and has regions varying in shape and/or translucency and/or coloration. The thickness of the translucent layer causes changes in the translucency attributes, and the distribution of the dye within the translucent layer influences the color perceived.

Advantageously, the prefabricated terminal subsurface can have color and translucency attributes which are similar to natural teeth. The large number of blanks must accordingly cover a sufficient number of variations in color and translucency of natural teeth.

Advantageously, the remaining surfaces of the blank which are to be machined can form part of a basic geometrical shape, in particular a cone, a cylinder, a cube, a cuboid, or a pyramid. Such basic geometrical shapes can be manufactured with justifiable technical effort and provide a sufficiently precise positional relationship of the surfaces of the blank.

When the method of the invention is implemented, it is advantageous when the surfaces of the blank which are to be machined have a known basic shape, for by this means the blanks themselves can be used as the basis for determination of the position of the blank in the machining equipment without having to provide additional calibration surfaces.

Advantageously, the positional relationship of the surfaces to be machined relative to each other, to the terminal subsurface, and to a holder on the blank can be known. By this means it is possible, by measuring the position of a plurality of points on the surface to be machined, to determine the position of the terminal subsurface with reference to the machining tool.

Advantageously, the surfaces to be machined can be embodied as reference surfaces for determination of the position. By this means it is possible to precede the machining operation by a calibration process with reference to the surface to be machined for determining the position thereof, in order to determine the position of the blank relative to the machining tool. Use can be made of a calibration technique, during which the surface property of the surface to be examined is impaired, i.e., in particular, when the surface is contacted with the removal of material therefrom.

Advantageously, the blank is made of plastics material or ceramics, preferably feldspar ceramics. These materials have been used with success in dental technology and are selected according to their attributes so as to fulfill the demands placed on the dental prosthetic item to be synthesized.

Advantageously, the blank can be composed of at least two layers differing from each other in color. Lamellar blanks are known in the prior art. The layers can be made of plastics material or ceramics, preferably feldspar ceramics. They can be parallel to each other and disposed along the longitudinal axis of the tooth. By this means it is possible to adapt the coloration, for example stepwise from cervical to incisal in a number of layers, to match the color gradient of natural teeth. If the material is itself translucent and the coloring matter is distributed in the material, the incident light is reflected from different depths of the colored material. The visual impression of color depth in natural teeth is imitated more efficiently in this way.

Advantageously, the prefabricated terminal subsurface can correspond, in the case of incisors, to the labial surface and preferably also to the incisor edge or, in the case of premolars, to the buccal surface and preferably also to the occlusal surface.

An assortment of blanks of the invention comprises a plurality of blanks at least of the same type but differing from each other in size, as described above. For each tooth having a specific tooth number according to the International Tooth Numbering System there is thus provided an assortment of blanks of various sizes and having prefabricated terminal subsurfaces of different shapes, coloration, and translucency attributes. A matching blank can then be selected from this assortment of blanks.

In the present invention, a tooth database for the production of dental prosthetic items, comprising at least one 3D model of a dental prosthetic item, is proposed. The 3D model of the dental prosthetic item has at least one terminal subsurface whose border line is fixed. A 3D model matching the preparation site is selected from the tooth database and can then be adjusted to the preparation site. This makes it easier to design the dental prosthetic item.

Advantageously, the 3D model is only available for adaptation outside the border line of the terminal subsurface for the purposes of designing the 3D model of the individual dental prosthetic item, whilst preferably a size-reducing adaptation in the marginal area of the terminal subsurface may be permissible. As opposed to finished teeth, this provides additional degrees of freedom for machining several different dental prosthetic items having the same prefabricated esthetic surface from one type of blank.

In the present invention, a database of blanks for the production of dental prosthetic items is proposed, which comprises at least one 3D model of a blank, which has at least one terminal subsurface having a fixed border line coincident with an esthetically relevant terminal subsurface of a 3D model of a tooth in a tooth database. The result of this measure is that when providing a dental prosthetic item starting from a 3D model of a tooth in the tooth database a terminal subsurface is provided which satisfies the esthetic demands and at least approximates the designed subregion of a 3D model of the planned dental prosthetic item.

Advantageously, each 3D model of the blank contains information on the border line for machining the terminal subsurface. By this means, when the 3D model of a tooth of a tooth database is adapted at least the central region of the terminal subsurface will be taken into account and can be left unchanged.

BRIEF DESCRIPTION OF THE DRAWINGS

Exemplary embodiments of the invention are illustrated in the drawings. In which

FIG. 2A is a top view of an almost finished dental prosthetic item carved from the blank shown in FIGS. 1A and 1B;

FIG. 2B is a sectional view of the machined blank shown in FIG. 2A taken along the line B-B;

FIG. 3A is a buccal side view of a blank for a premolar;

FIG. 3B is a top view of the blank shown in FIG. 3a;

FIG. 4A is a buccal side view of an almost finished dental prosthetic item carved from the blank shown in FIGS. 3A and 3B;

FIG. 4B is a top view of the machined blank shown in FIG. 4A;

FIG. 6A is a top view of an almost finished dental prosthetic item carved from the blank shown in FIG. 5A;

FIG. 6B is a sectional view of the machined blank of FIG. 6A taken along the line D-D;

DETAILED DESCRIPTION OF EXEMPLARY EMBODIMENTS OF THE INVENTION

Figures 1A, 1B:
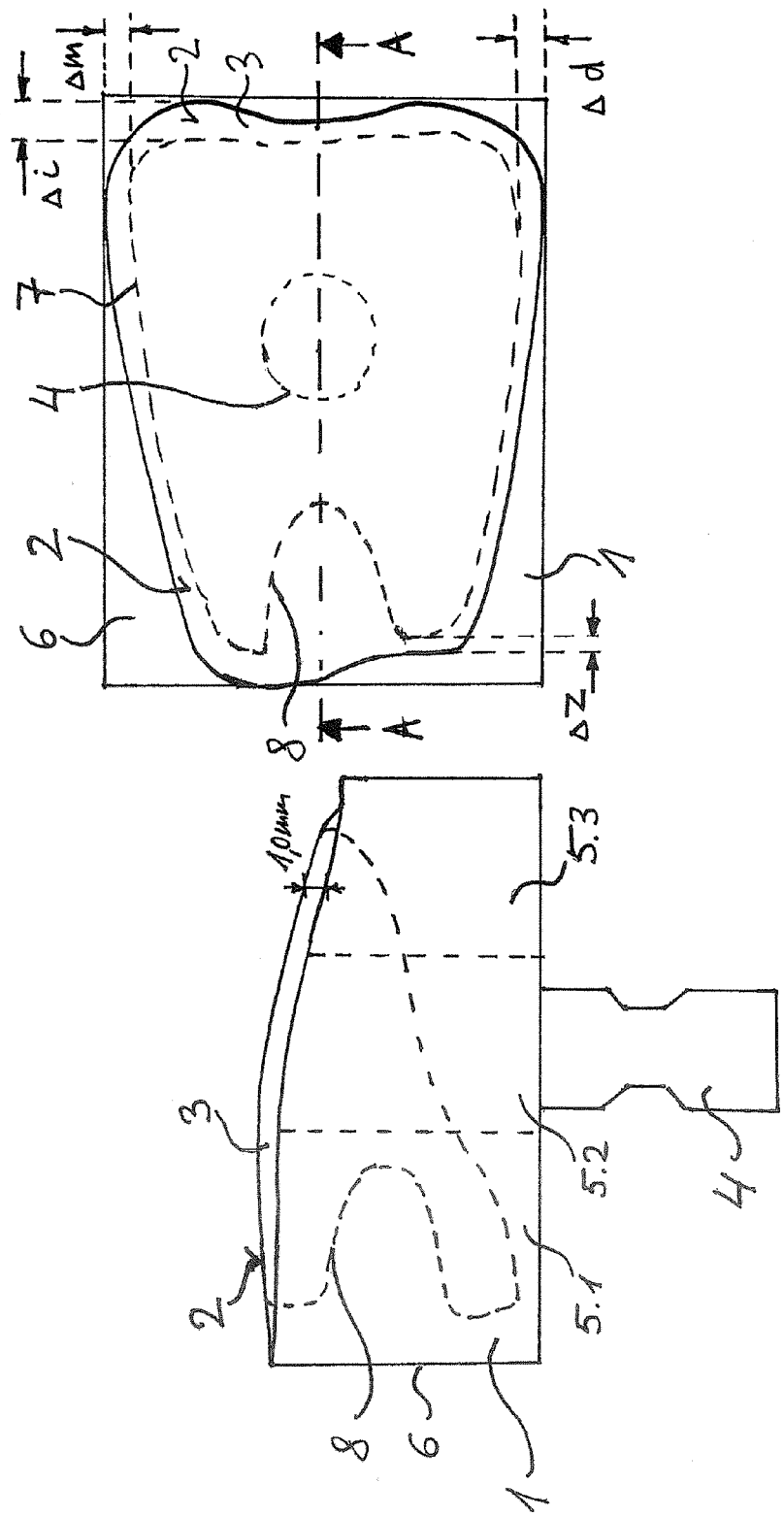
FIG. 1A is a top view of a blank for an incisor.
FIG. 1B is a sectional view of the blank shown in FIG. 1A taken along the line A-A of FIG. 1A.

FIG. 1A is a top view of a blank 1 for the production of a dental prosthetic item for an incisor and FIG. 1B is a sectional view taken along the line A-A. The blank 1 has a prefabricated terminal subsurface 2, which is disposed on a translucent layer 3. The prefabricated terminal subsurface 2 corresponds in shape to a lower right-hand incisor having tooth number 41 according to the International Tooth Numbering System. The blank 1 comprises a holder 4 for fitting the blank 1 into machining equipment (not shown).

The prefabricated terminal subsurface 2 has the shape of a labial surface of an incisor. The translucent layer 3 has a maximum thickness of 1 mm at the incisal end of the prefabricated surface and as a result, the prefabricated terminal subsurface 2 disposed over the translucent layer 3 has similar translucency attributes to those of natural incisal teeth.

The blank 1 can be made of feldspar ceramics and consist of three layers 5.1, 5.2, and 5.3 having different color attributes, the layers 5.1 to 5.3 being designed and arranged so as to imitate the color gradient of natural incisal teeth as far as possible. Lamellar blanks showing different colors are known in the prior art. The surfaces 6 to be machined are part of a rectangular cuboid but can alternatively be of some other basic geometrical shape, in particular a cone, cylinder or pyramid.

The positional relationship of the surfaces 6 to be machined relative to the holder 4 and to the terminal subsurface 2 is known. For this reason, it is possible, according to the invention, to determine the position of the blank and thus of the terminal subsurface 2 relative to the machining tool by measuring the position at various points on the surfaces 6.

Within the terminal subsurface 2 there is shown a designed subregion 7 of a planned dental prosthetic item, which exists in the form of a digital 3D model. This designed subregion 7 is spaced at the incisal edge by a distance $\Delta i$, at the cervical edge by a distance $\Delta z$, at the mesial edge by a distance $\Delta m$ and at the distal edge by a distance $\Delta d$. In the cervical surface, the planned dental prosthetic item has a lumen 8 serving for connection to a prepared tooth stump (not shown). The blank 1 can thus be selected from an assortment such that the designed subregion 7 approximately coincides with the inner region of the prefabricated terminal subsurface 2.

FIG. 2A is a top view of the labial side of a dental prosthetic item 10 for an incisor which has been carved from the blank illustrated in FIG. 1A, and FIG. 2B is a sectional view of the dental prosthetic item 10 taken along the line B-B in FIG. 2A. From the blank shown in FIGS. 1A and 1B there have automatically been carved a cervical surface 11 having a lumen 8, an incisor edge 12, a mesial surface 13, a distal surface 14, and a lingual surface 15, whilst the terminal subsurface 2 has not been machined inside the border line of the designed subregion 7 of FIGS. 1A and 1B, which corresponds to the labial surface 16.

At the edge of the labial surface 16 the prefabricated terminal subsurface 2 having the translucent layer 3 was machined during the grinding operation and can then be polished, in order to create an optically uniform transition between the unground labial surface 16 and the remaining ground surfaces 12 to 14.

FIG. 3A is a buccal side view of a blank 20 for the production of a dental prosthetic item for a premolar and FIG. 3B is an occlusal top view of said blank 20. The blank 20 contains a prefabricated terminal subsurface 2 on a translucent layer 3. The prefabricated terminal subsurface 2 is in the shape of a buccal surface 21 and an occlusal surface 22 of a lower right-hand premolar with the tooth number 45 according to the International Tooth Numbering System. The translucent layer 3 can have a maximum thickness of 1.5 mm. The blank 20 can be made of feldspar ceramics and consist of three layers 5.1, 5.2, and 5.3 having different color attributes such that the color gradient of natural premolars is imitated as far as possible. The surfaces 6 to be machined again form a rectangular cuboid.

Within the terminal subsurface 2 there is shown a designed subregion 7 of the planned dental prosthetic item, while the occlusal surface 22 and the major portion of the buccal surface 21 remain unchanged. This designed subregion 7 is spaced at the cervical edge by a distance Δz, at the mesial edge by a distance Δm and at the distal edge by a distance Δd from the edge of the terminal subsurface 2. In the cervical surface, the planned dental prosthetic item has a lumen 8 serving for connection to a prepared tooth stump (not shown). The prefabricated occlusal surface 22 comprises fissures 23 which give an optical impression similar to that given by a natural premolar.

FIG. 4A is a buccal side view of a dental prosthetic item 30 as carved from the blank shown in FIG. 3A, and FIG. 4B is an occlusal top view of said dental prosthetic item 30.

During the machining operation, there was carved from the blank shown in FIG. 3A a cervical surface 31 having a lumen 8 in the interior of the dental prosthetic item 30, represented by a dashed line, a mesial surface 32, a distal surface 33, and a lingual surface 34, represented by shading, while the terminal subsurface 2 enclosed by the periphery of the designed subregion 7, comprising the buccal surface 21 and the occlusal surface 22 was not machined and a cylindrical connecting bar 35 adapted to connect the dental prosthetic item 30 to the holder 4 was left unchanged. The machined translucent layer 3 at the edge of the designed subregion 7 can then be polished, in order to impart the desired translucency property in the marginal area of the designed subregion 7.

Figures 5A, 5B:
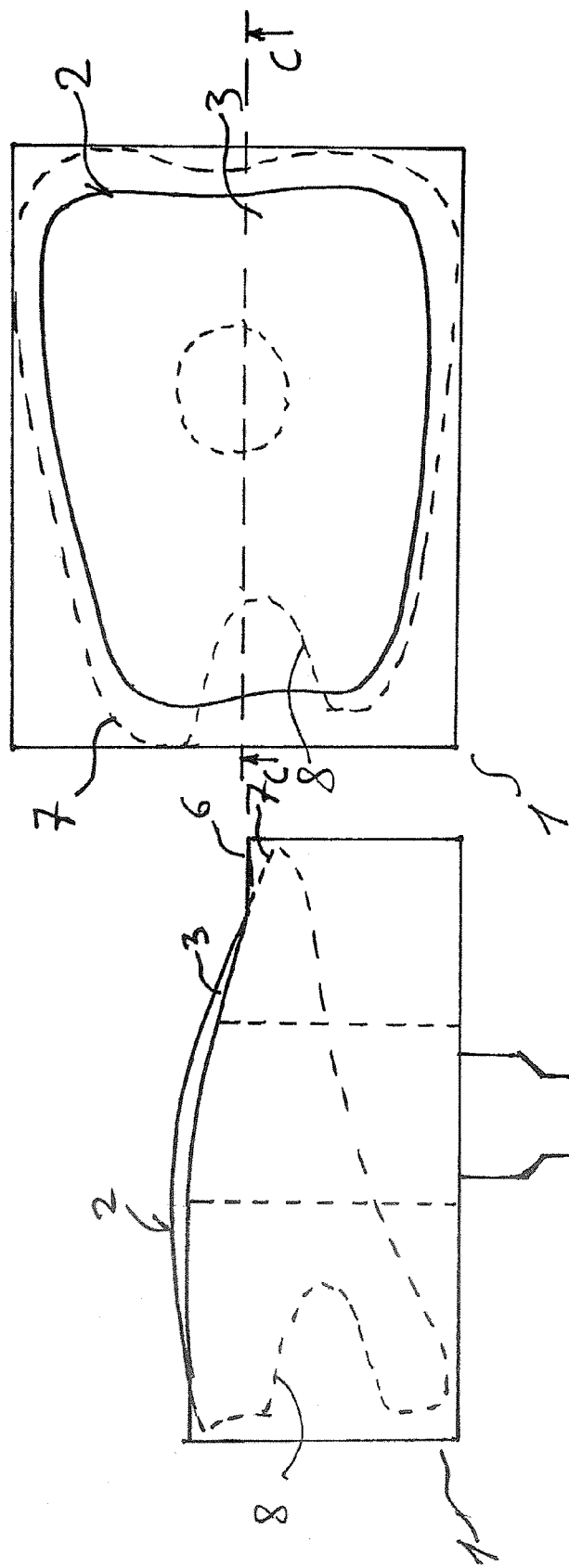
FIG. 5A is a top view of a blank for an incisor having a designed subregion extending beyond a terminal subsurface.
FIG. 5B is a sectional view of the blank shown in FIG. 5A taken along the line C-C.

FIG. 5A is a top view of a blank 1 for the production of a dental prosthetic item for an incisor having a designed subregion 7 extending beyond the terminal subsurface 2, and FIG. 5B is a cross-section of said blank 1. Thus the prefabricated terminal subsurface 2 disposed on the translucent layer 3 is smaller than in FIG. 1 and the planned designed subregion 7 of the dental prosthetic item to be produced surrounds the terminal subsurface 2. In the machining operation, the blank 1 is machined down to the terminal subsurface 2.

FIG. 6A is a top view of a dental prosthetic item 10 as carved from the blank shown in FIG. 5A, and FIG. 6B is a sectional view of the blank shown in FIG. 6A taken along the line D-D. During the grinding operation, the marginal area 40 between the prefabricated terminal subsurface 2 and the designed subregion 7, shown as a shaded area in FIG. 6A, was ground down and consequently no longer has a translucent layer. To recover the translucency attribute in marginal area 40, the marginal area 40 is subsequently veneered with a translucent layer 41, shown in FIG. 6B as a shaded area.

Figure 7:
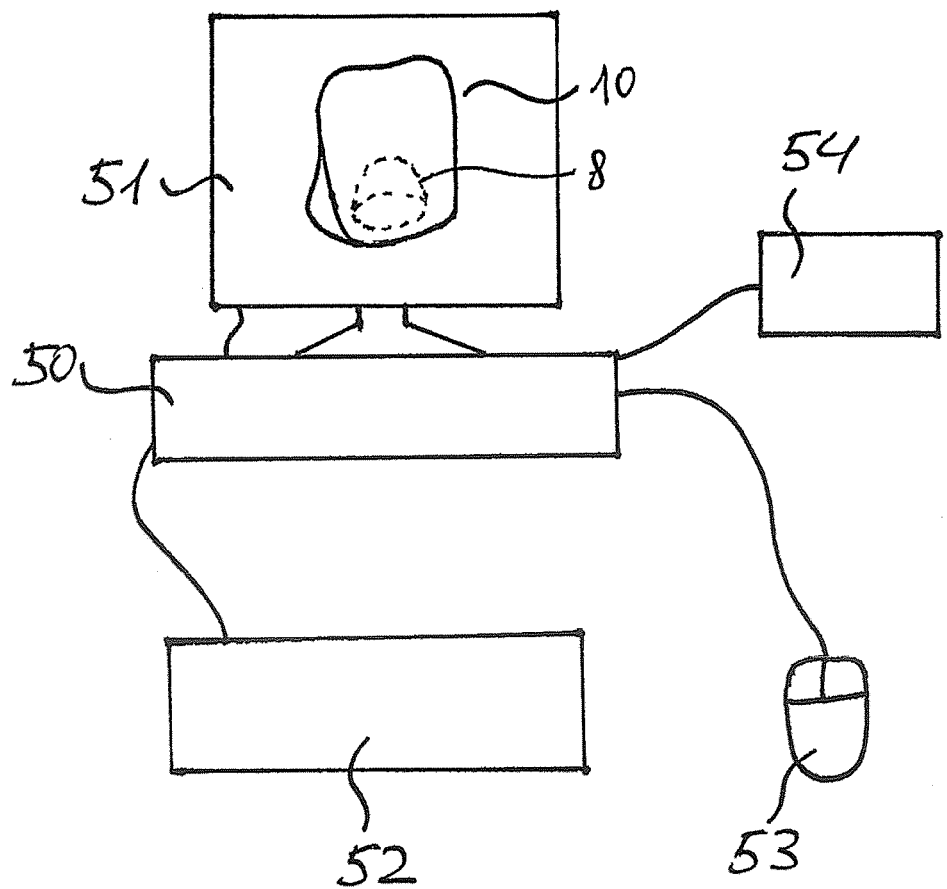
FIG. 7 shows equipment for carrying out the method.

FIG. 7 shows a computer 50 equipped with a display unit 51, a computer keyboard 52, a computer mouse 53, and a memory device 54. The display unit 51 shows a 3D model of a planned dental prosthetic item 10 for an incisor having a lumen 8. The computer 50 can serve for data processing when designing the 3D model of the dental prosthetic item to be produced and when planning the production of the dental prosthetic item 10, 30 (FIG. 2, FIG. 4, FIG. 6). The designed subregion 7 (FIG. 2, FIG. 4, FIG. 6) of the planned dental prosthetic item is selected optionally either manually by the user using input means 3 and 4 or automatically by means of the computer 1. From the position of the dental prosthetic item in the oral cavity of the patient it is possible, with the aid of computer 1 using computer algorithms, to simulate the incident light through the oral opening and to automatically determine the surface which will be visible from outside and which is designated as the designed subregion 7 (FIG. 2, FIG. 4, FIG. 6) of the dental prosthetic item. Another possible embodiment is one in which the designed subregion 7 (FIG. 2, FIG. 4, FIG. 6) can be automatically determined with reference to library data concerning other 3D models which have already been planned and stored in the storage device 5 and have selected designed subregions of dental prosthetic items for the corresponding tooth of a specific tooth number.

A blank 1, 20 having a prefabricated terminal subsurface 2 (FIG. 1, FIG. 3, FIG. 5) is automatically selected by the computer 50 or manually by the user using input means 52 and 53 such that the terminal subsurface 2 has a shape which at least approximates the selected designed subregion 7 of the planned dental prosthetic item. The 3D model of the planned dental prosthetic item can be displayed on the display unit 2 within the 3D model of the selected blank 1, 20 and positioned such that the designed subregion 7 coincides with the terminal subsurface 2 as far as possible. Furthermore a positional relationship can be determined, in order to match the specified terminal subsurface to the 3D model.

Subsequently, a machining schedule is automatically computed, in order to machine the planned dental prosthetic item 10, 30 (FIG. 2, FIG. 4, FIG. 6) from the selected blank 1, 10.

Figure 8:
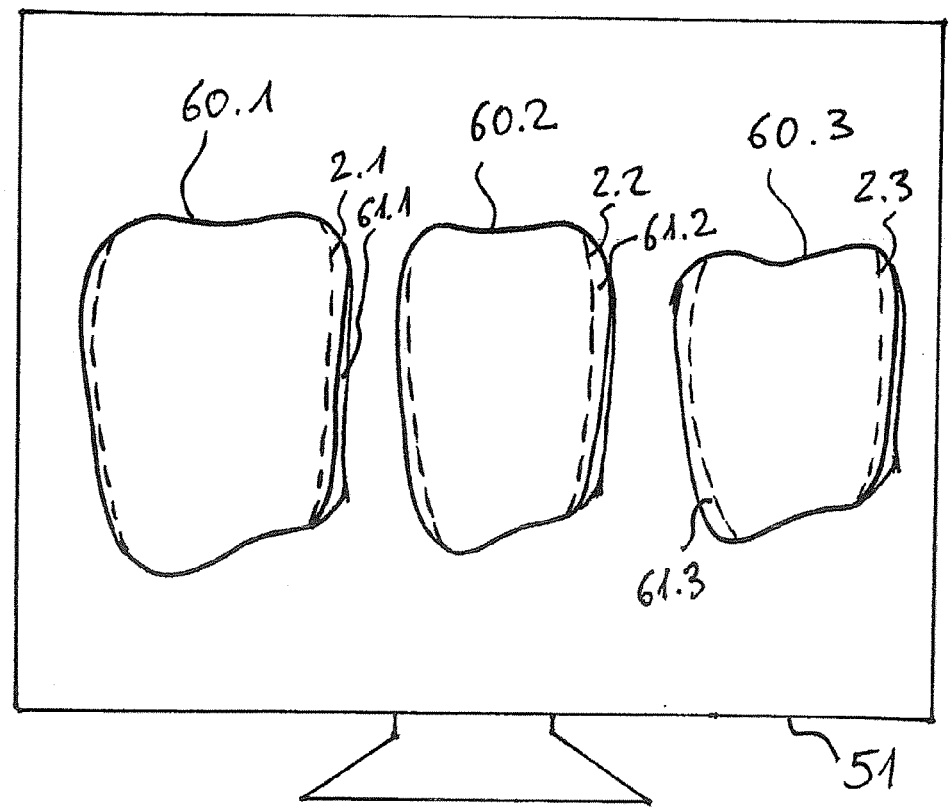
FIG. 8 shows 3D models of teeth in a tooth database as displayed by means of a display unit.

FIG. 8 shows three 3D models 60.1, 60.2, and 60.3 of teeth in a tooth database, which are displayed by the display unit 51, the tooth database being stored in the memory device 54. The 3D models 60.1, 60.2, and 60.3 of teeth of different sizes and shapes represent possible variants of a tooth having the tooth number 41 according to the International Tooth Numbering System. The 3D models 60.1, 60.2, and 60.3 exhibit defined esthetically relevant terminal subsurfaces 2.1, 2.2, and 2.3, which differ in planned attributes such as shape, coloration, and translucency. The remaining areas 61.1, 61.2, and 61.3 lying outside of the terminal subsurfaces 2.1, 2.2, and 2.3 differ in their shape resembling the shape of natural teeth. In the method of the invention, a 3D model 60.1 to 60.3 matching the preparation site is selected from the 3D models in the tooth database having the required terminal subsurfaces 2.1 to 2.3. Subsequently, the selected 3D model is changed for adaptation to the individual tooth situation at the preparation site such that the required terminal subsurface 2.1 to 2.3 remains unchanged in at least a central region thereof. By this means there is formed an individual 3D model adjusted to the preparation site of the dental prosthetic item to be synthesized and having a designed subregion which at least approximates the terminal subsurface of a blank.

Figure 9:
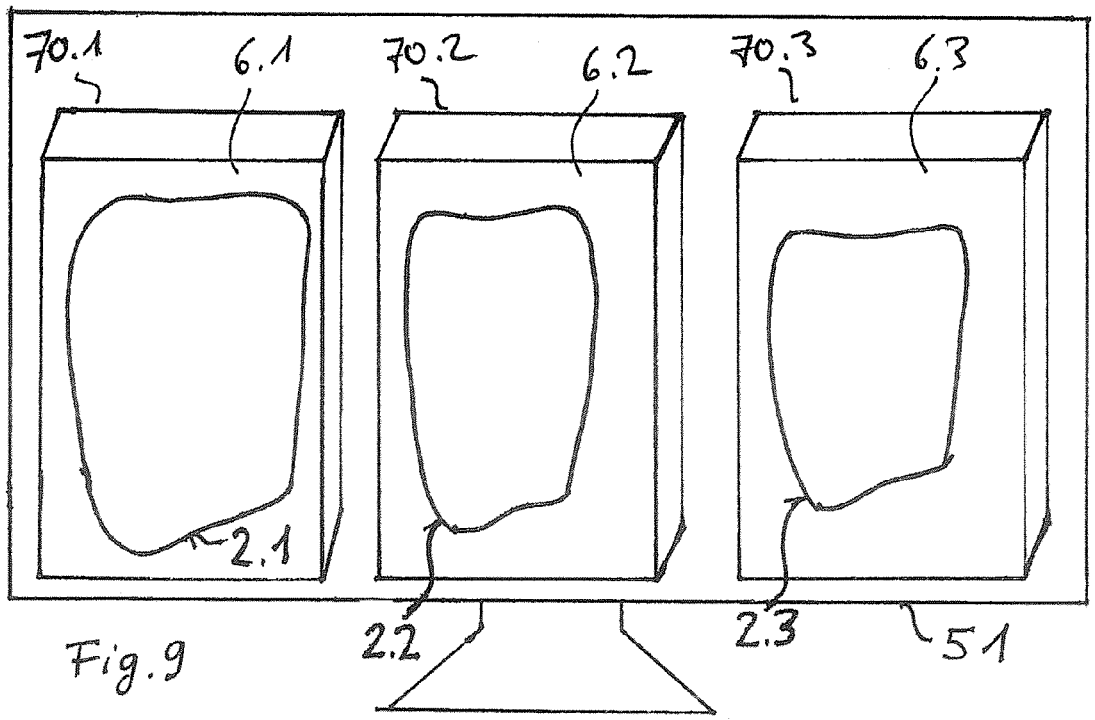
FIG. 9 shows 3D models of blanks in a database of blanks, displayed by means of a display unit and corresponding to the tooth database shown in FIG. 8.

FIG. 9 shows three 3D models of blanks 70.1, 70.2, and 70.3 in a database of blanks which have been stored in the memory device 54 of FIG. 7 and are displayed on the display unit 51. The 3D models 70.1, 70.2, and 70.3 in the database of blanks correspond to 3D models 60.1, 60.2, and 60.3 in the tooth database and exhibit coincident terminal subsurfaces 2.1, 2.2, and 2.3. The positional relationship of surfaces 6.1, 6.2, and 6.3 to be machined relative to each other and to the terminal subsurfaces 2.1, 2.2, and 2.3 is known. Knowing the surface data of a 3D model of the dental prosthetic item and the surface data of the 3D model of the blank from which the dental prosthetic item is to be machined, it is possible to create a machining schedule for the machining tool.

Figure 10:
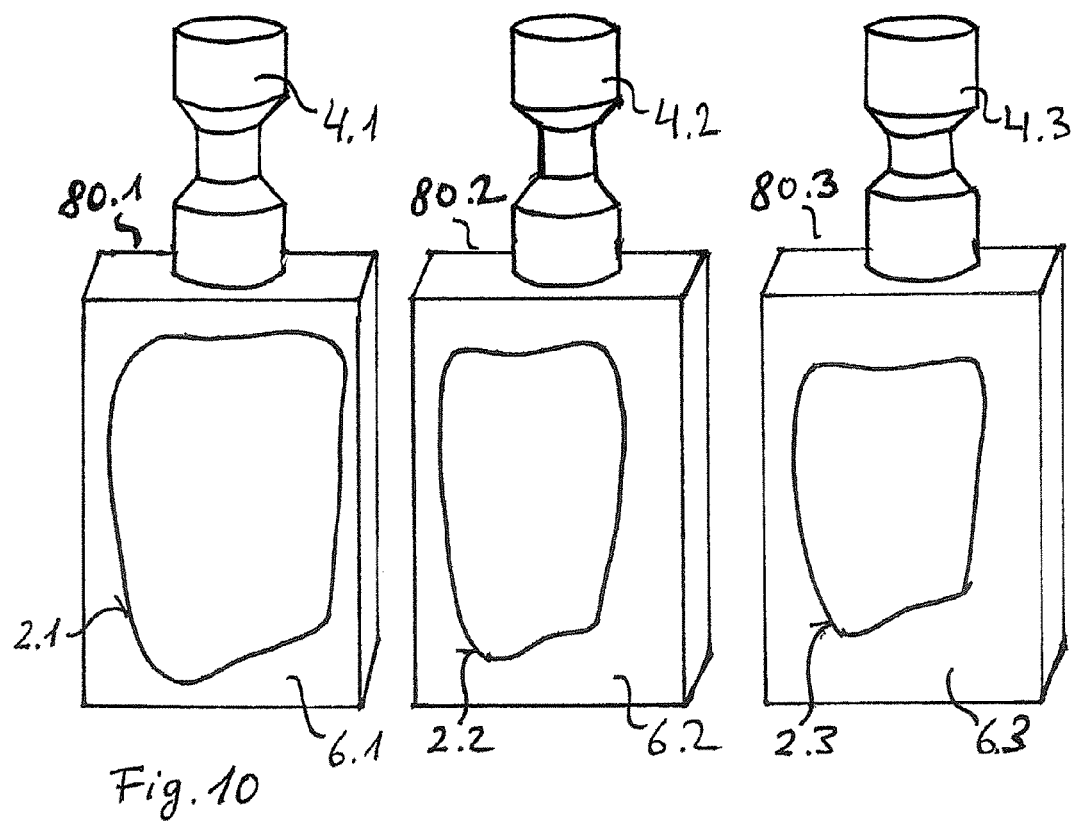
FIG. 10 shows blanks of an assortment of blanks corresponding to the 3D models of blanks shown in FIG. 9.

FIG. 10 shows three blanks 80.1, 80.2, and 80.3 of the assortment of blanks produced according to the 3D models 70.1, 70.2, and 70.3 in the database of blanks. The blanks 80.1 to 80.3 exhibit surfaces 6.1, 6.2, and 6.3 to be machined and holders 4.1, 4.2, and 4.2 for clamping said blanks in the machining equipment. In the method of the invention, the dental prosthetic item is carved from a blank in the assortment of blanks which has a terminal subsurface which coincides with the terminal subsurface 2.1, 2.2, and 2.3 of selected tooth 60.1, 60.2, and 60.3 in the tooth database. Following machining, the terminal subsurface 2.1, 2.2, and 2.3 remains unchanged at least in a central region thereof. The positional relationship of the surfaces 6.1 to 6.3 to be machined relative to each other and to the terminal subsurfaces 2.1 to 2.3 and to holders 4.1 to 4.3 is known. Prior to the machining operation, a calibration process for determining the position of the blank is carried out. The position of at least three points on different surfaces 6.1 to 6.3 to be machined, which in this case form part of a basic cuboid shape, is determined relative to the machining equipment. Subsequently, the positional relationship of the terminal subsurface 2.1 to 2.3 relative to the machining equipment is derived from the known positional relationship of surfaces 6.1 to 6.3 to be machined to the holder 4.1 to 4.3 and of the holder 4.1 to 4.3 to the machining equipment.

LIST OF REFERENCE NUMERALS OR CHARACTERS

1 blank
2 terminal subsurface
3 translucent layer
4 holder
5 layers showing different color attributes
6 surfaces to be machined
7 designed subregion
8 lumen
10 dental prosthetic item for an incisor
11 cervical surface
12 incisor edge
13 mesial surface
14 distal surface
15 lingual surface
16 labial surface
20 blank
21 buccal surface
22 occlusal surface
23 lumen
24 fissures
30 dental prosthetic item for a premolar
31 cervical surface
32 mesial surface
33 distal surface
34 lingual surface
35 connecting bar
40 edge of the designed subregion
41 translucent layer
50 computer
51 display unit
52 computer keyboard
53 computer mouse
54 memory device
60.1-60.3 3D models of teeth
61.1-61.3 remaining areas
2.1-2.3 terminal subsurfaces
70.1-70.3 3D models of blanks
6.1-6.3 surfaces to be machined
4.1-4.2 holder
80.1-80.3 blanks
$\Delta i$ incisal distance
$\Delta z$ cervical distance
$\Delta m$ mesial distance
$\Delta d$ distal distance

The invention claimed is:

1. A method for producing a dental prosthetic item, the method comprising:
providing a 3D model of the dental prosthetic item, wherein providing the 3D model comprises determining an esthetically relevant designed subregion of a 3D model of the dental prosthetic item as part of an exterior surface of the dental prosthetic item, at least part of the esthetically relevant designed subregion of the 3D model of the dental prosthetic item corresponds to a surface of the dental prosthetic that is visible from outside an oral cavity when the dental prosthetic item is installed in the oral cavity, and the esthetically relevant designed subregion of the 3D model of the dental prosthetic item corresponds (i) in a case of incisors, to at least one of a labial surface and an incisor edge and (ii) in a case of premolars, to at least one of a buccal surface and an occlusal surface;
selecting a suitable blank from a plurality of possible blanks;
specifying a blank from a plurality of blanks having a prefabricated esthetically relevant terminal subsurface of a surface of a tooth, a terminal subsurface of said blank being approximating a shape of the esthetically relevant designed subregion and the prefabricated esthetically relevant terminal subsurface being a part of the terminal subsurface; and
forming the dental prosthetic item from the selected blank such that the prefabricated terminal subsurface of said blank remains unmachined in at least a central region thereof, wherein the forming of the prosthetic dental item includes machining the blank only in a marginal area of the terminal subsurface and on at least some surfaces outside of the terminal subsurface.

2. The method as defined in claim 1, wherein the step of providing a 3D model further comprises:
selecting a 3D model of a tooth matching a preparation site from a tooth database having a plurality of 3D models of a tooth having at least one desired esthetically relevant terminal subsurface, wherein for each 3D model of a tooth in the tooth database there is present, in a database of blanks, a 3D model of a blank having a terminal subsurface coinciding with the terminal subsurface of the tooth; and
changing the 3D model selected for adaptation to at least one predetermined tooth at the preparation site from an assortment of blanks matching the database of blanks exists,
wherein the step of forming forms the 3D model from the blank corresponding to the 3D model of the at least one tooth.

3. The method as defined in claim 1, wherein the determining is performed either interactively by a user operating a user interface, or automatically.

4. The method as defined in claim 3, wherein the selecting of the blank includes selecting a blank having a terminal subsurface from a plurality of blanks having at least one prefabricated terminal subsurface of a tooth surface is performed automatically, and deviations between the esthetically relevant designed subregion on the 3D model of the dental prosthetic item and the prefabricated terminal subsurface are minimized.

5. The method as defined in claim 4, wherein minimizing of the deviations is carried out in such a manner that the deviations are located primarily in the marginal area of the esthetically relevant designed subregion.

6. The method as defined in claim 3, wherein the forming is performed such that a finished dental prosthetic item at least one subregion of the prefabricated terminal subsurface of the blank takes the place of the esthetically relevant designed subregion of the 3D model of the dental prosthetic item.

7. The method as defined in claim 3, further comprising determining a positional relationship between the esthetically relevant designed subregion of the 3D model of the dental prosthetic item and the prefabricated terminal subsurface of the blank.

8. The method as defined in claim 3, wherein the positional relationship is used as a basis for determination of a machining schedule for the selected blank.

9. The method as defined in claim 1, wherein the blank exhibits a translucent layer and the prefabricated terminal subsurface is disposed on the translucent layer.

10. The method as defined in claim 9, wherein the prefabricated terminal subsurface of the blank comprises the esthetically relevant designed subregion of the dental prosthetic item, and wherein the method further comprises machining the terminal subsurface extending over the translucent layer down to the esthetically relevant designed subregion, and polishing a machined edge of the translucent layer.

11. The method as defined in claim 9, wherein the esthetically relevant designed subregion of the dental prosthetic item comprises the prefabricated terminal subsurface of the blank, and wherein the method further comprises veneering a remaining marginal area between the prefabricated terminal subsurface and the esthetically relevant designed subregion, which initially exhibits no translucent layer, and polishing the remaining marginal area.

12. The method as defined in claim 1, wherein surfaces to be machined outside a terminal subsurface of the blank exceed the size of the surface of the dental prosthetic item by at least 1 mm.

13. The method as defined in claim 1, wherein the esthetically relevant designed subregion corresponds to a surface being visible when a mouth is open after insertion of said dental prosthetic item.

14. The method as defined in claim 1, wherein the esthetically relevant designed subregion covers not more than 50% of an entire exterior surface of the 3D model of the dental prosthetic item.

15. The method as defined in claim 1, wherein the blank is selected from a large number of blanks, which have prefabricated terminal subsurfaces showing at least one member selected from the group consisting of deviating shapes, coloration, and translucency attributes.

\* \* \* \* \*